United States Patent
Honma et al.

[11] Patent Number: 6,069,166
[45] Date of Patent: May 30, 2000

[54] FUSED HETEROCYCLIC BENZENECARBOXAMIDE DERIVATIVES AND PGD$_2$ ANTAGONISTS COMPRISING THEM

[75] Inventors: Tsunetoshi Honma, Nara; Yoshiharu Hiramatsu; Akinori Arimura, both of Osaka, all of Japan

[73] Assignee: Shionogi & Co., Ltd., Osaka, Japan

[21] Appl. No.: 09/319,022

[22] PCT Filed: Dec. 10, 1997

[86] PCT No.: PCT/JP97/04526

§ 371 Date: May 28, 1999

§ 102(e) Date: May 28, 1999

[87] PCT Pub. No.: WO98/25915

PCT Pub. Date: Jun. 18, 1998

[30] Foreign Application Priority Data

Dec. 12, 1996 [JP] Japan ..................... 8-331962

[51] Int. Cl.$^7$ .......................... A61K 31/38; A61K 31/34; C07D 333/74; C07D 333/56; C07D 307/91
[52] U.S. Cl. .......................... 514/443; 514/468; 514/469; 549/43; 549/57; 549/461; 549/470
[58] Field of Search ................ 549/57, 43, 461, 549/470; 514/443, 468, 469

[56] References Cited

U.S. PATENT DOCUMENTS

| | | | |
|---|---|---|---|
| 4,389,413 | 6/1983 | Hamanaka et al. ................... | 424/305 |
| 4,792,550 | 12/1988 | Miyake et al. | |
| 4,904,819 | 2/1990 | Hagishita et al. ................... | 560/118 |
| 5,168,101 | 12/1992 | Arai et al. | |
| 5,728,846 | 3/1998 | Vuligonda et al. ................. | 549/16 |
| 5,763,609 | 6/1998 | Yuan et al. ............................ | 544/363 |
| 5,929,107 | 7/1999 | Natsugari et al. ................... | 514/443 |

FOREIGN PATENT DOCUMENTS

| | | |
|---|---|---|
| 0 171 146 | 2/1986 | European Pat. Off. |
| 0 226 346 | 6/1987 | European Pat. Off. |
| 0 290 285 | 11/1988 | European Pat. Off. |
| 0 837 052 | 2/1998 | European Pat. Off. |

OTHER PUBLICATIONS

Seno, K., et al., "Thromboxane A$_2$ Receptor Antagonist. III. Synthesis and Pharmacological Activity of 6,6-Dimethylbicyclo[3.1.1]heptane Derivatives with a Substituted Sulfonylamino Group at C-2", Chem. Pharm. Bull., vol. 37, No. 6, pp. 1524–1533 (1989).

Tsuri, T., et al., "Bicyclo[2.2.1]heptane and 6,6-Dimethylbicyclo[3.1.1]heptane Derivatives: Orally Active, Potent, and Selective Prostaglandin D$_2$ Receptor Antagonists," J. Med. Chem., vol. 40, pp. 3504–3507 (1997).

Martin-Smith, M., et al., "Benzo[β]thiophen Derivatives. Part VI. The Syntheses of 3-(2-Amino-ethyl)-5-hydroxybenzo[β]thiophen and Related Compounds," J. Chem. Soc., Section C, pp. 1898–1905 (1967).

*Primary Examiner*—Deborah C. Lambkin
*Attorney, Agent, or Firm*—Foley & Lardner

[57] ABSTRACT

A compound, pharmaceutically acceptable salt thereof, or hydrate thereof having a PGD$_2$-antagonistic activity, and an inhibitory activity against infiltration of eosinophils, useful for treating mast cell dysfunction-associated diseases, such as systemic mastocytosis and disorder of systemic mast cell activation, as well as tracheal contraction, asthma, allergic rhinitis, allergic conjunctivitis, urticaria, ischemic reperfusion injury, inflammation and atopic dermatitis, which is shown by the formula (I):

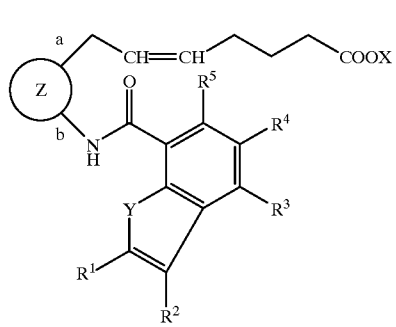

is provided.

18 Claims, 1 Drawing Sheet

FUSED HETEROCYCLIC BENZENECARBOXAMIDE DERIVATIVES AND PGD$_2$ ANTAGONISTS COMPRISING THEM

This application is a 371 of PCT/JP97/04526 filed Dec. 10, 1997.

FIELD OF THE INVENTION

The present invention relates to fused heterocyclic benzenecarboxamide derivatives, pharmaceutical compositions comprising them, PGD$_2$ (prostaglandin D$_2$) antagonists comprising them and drugs for treating nasal blockage comprising them.

BUCKGROUND OF THE INVENTION

Some of bicyclic amide derivatives analogous to the compounds of the present invention have been described as thromboxane A$_2$ (TXA$_2$) antagonists (Japanese Patent Publication (Kokoku) No. 53295/1991). However, in the Japanese Patent Publication (Kokoku) No. 53295/1991, it has only been described that the compounds are useful as TXA$_2$ antagonists, but there is no suggestion of usefulness thereof as PGD$_2$ antagonists as found in the present invention. On the other hand, in Japanese Patent Publication (Kokoku) No.79060/1993, Japanese Patent Publication (Kokoku) No.23170/1994 and Chem. Pharm. Bull. Vol.37, No.6 1524–1533 (1989), bicyclic amide derivatives have been described as intermediates for bicyclic sulfonamide derivatives. However, the compounds disclosed therein are different from those of the present invention in the types of substituents at the amide portion. And some of the compounds analogous to the compounds of the present invention have been described as PGD$_2$ antagonists in WO 97/00853. However, there is no suggestion that the compounds disclosed in WO 97/00853 possess a inhibitory activity against infiltration of eosionophils.

TXA$_2$ has been known to have various activities such as platelet aggregation, thrombogenesis, etc. The TXA$_2$ antagonists which compete with TXA$_2$ have therefore been considered to be useful as anti-thrombotic agents as well as medicines to be used in the treatment of myocardial infarction or asthma. On the other hand, the PGD$_2$ antagonists of the present invention are useful for the improvement of conditions caused by excessive production of PGD$_2$, particularly as drugs for treating diseases in which mast cell dysfunction is involved, for example, systemic mastocytosis and disorder of systemic mast cell activation as well as tracheal contraction, asthma, allergic rhinitis, allergic conjunctivitis, urticaria, ischemic reperfusion injury, inflammation, and atopic dermatitis.

PGD$_2$ is a major prostanoid that is produced in and released from mast cells in which it is produced through PGG$_2$ and PGH$_2$ from arachidonic acid by the action of cyclooxygenase activated by immunological or unimmunological stimulation. PGD$_2$ has various potent physiological and pathological activities. For example, PGD$_2$ can cause strong tracheal contraction to lead to bronchial asthma, and in a systemic allergic state, it dilates the peripheral vessels to cause an anaphylactic shock. Especially, much attention has been paid to the theory that PGD$_2$ is one of the causal substances responsible to the onset of nasal blockage in the allergic rhinitis. Therefore, it has been proposed to develop an inhibitor against the biosynthesis of PGD$_2$ or an antagonist of PGD$_2$ receptor as a drug for the reduction of nasal blockage. However, the inhibitor of PGD$_2$ biosynthesis possibly much affects the synthesis of prostaglandins in other parts of organisms, and therefore, it is desirable to develop an antagonist (blocker) specific to the PGD$_2$ receptor.

DISCLOSURE OF THE INVENTION

The present inventors have studied intensively to develop PGD$_2$ receptor antagonists (blockers) specific to the PGD$_2$ receptor, and found that a series of compounds of the formula (I) below, pharmaceutically acceptable salts thereof, or hydrates thereof possess a potent activity as PGD$_2$ receptor antagonists and a inhibitory activity against infiltration of eosionophils, and are useful as drugs for treating nasal blockage. The compounds of the present invention having PGD$_2$ antagonist activity are different from the known TXA$_2$ antagonists in the active site and mechanism, application, and character.

Accordingly, the present invention provides a compound of the formula (I):

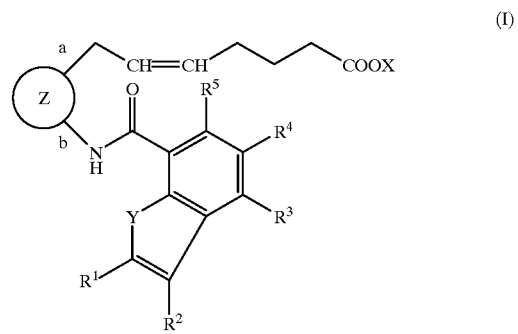

wherein

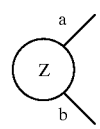

represents

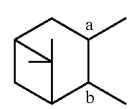

(A)

OR

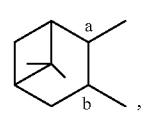

(B)

$R^1$, $R^2$, $R^3$, $R^4$ and $R^5$ represent independently hydrogen, alkyl, alkoxy, alkylthio, hydroxy, halogen, acyloxy or optionally substituted amino, or $R^1$ and $R^2$ may form an optionally substituted carbon ring together with the adjacent carbon atoms, $R^3$ and $R^4$ may form an optionally substituted carbon ring or an optionally substituted thiophene together with the adjacent carbon atoms, or $R^4$ and $R^5$ may form an optionally substituted carbon ring together with the adjacent carbon atoms, Y represents O or S, X represents hydrogen or alkyl, and the double bond on the α-chain has E configuration or Z configuration, pharmaceutically acceptable salt thereof, or hydrate thereof.

In the present specification, the linkage in the formula (I) represented by the group:

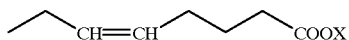

wherein X is as defined above;
is referred to as α-chain, the linkage represented by the group:

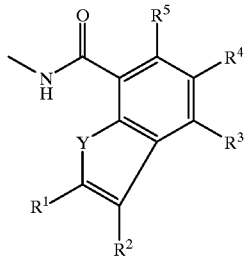

wherein $R^1$, $R^2$, $R^3$, $R^4$, $R^5$ and Y are as defined above;
is referred to as ω-chain.

The double bond on the α-chain has E configuration or Z configuration.

Figure 1:
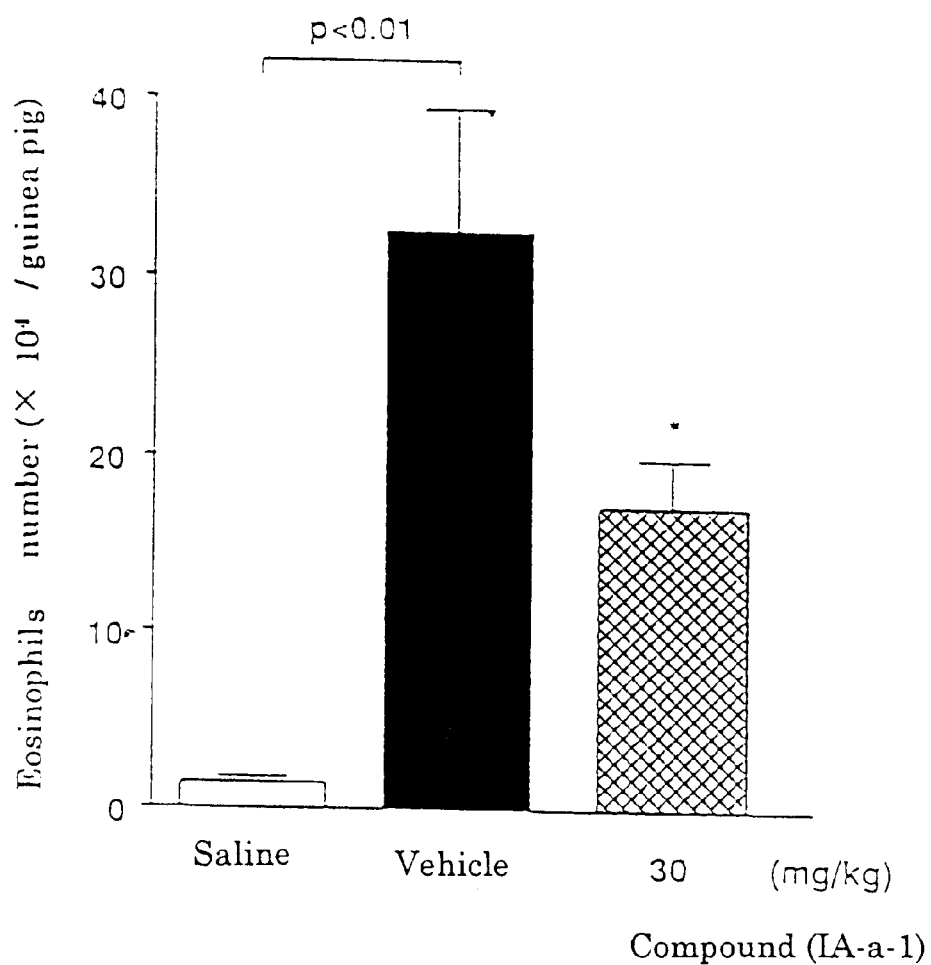
FIG. 1 shows the activity of the compound (IA-a-1) against infiltration of eosinophils in the nasal cavity induced by an antigen.

In the FIGURE, the white column indicates a group to which saline was inhaled instead of ovalbumin; the black column indicates a group to which an antigen was inhaled to induce an inflammatory reaction but not administered the compound (IA-a-1); and the gray columns indicate groups to which an antigen was inhaled to induce an inflammatory reaction and administered the compound (IA-a-1). The asterisk * indicate significant difference from vehicle at p<0.05.

BEST MODE FOR CARRYING OUT THE INVENTION

The compounds (I) can be specifically exemplified by a compound of the formula (IA):

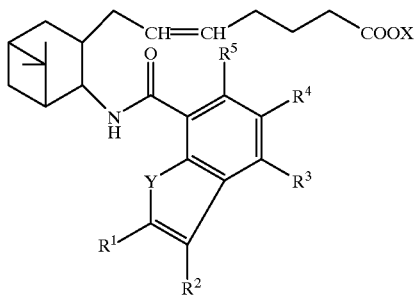

wherein $R^1$, $R^2$, $R^3$, $R^4$, $R^5$, Y and X are as defined above, and the double bond on the α-chain has E configuration or Z configuration, pharmaceutically acceptable salt thereof, or hydrate thereof.

Similarly, the compounds (I) can also be exemplified by the compound of the formula (IB):

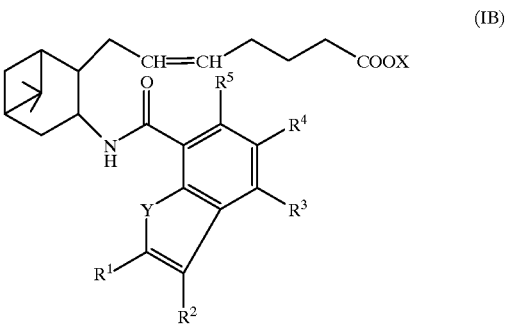

wherein $R^1$, $R^2$, $R^3$, $R^4$, $R^5$, Y and X are as defined above, and the double bond on the α-chain has E configuration or Z configuration, pharmaceutically acceptable salt thereof, or hydrate thereof.

More specifically, the compounds of the formula (IA) can be exemplified by:

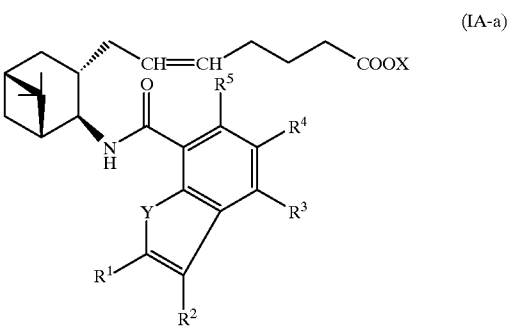

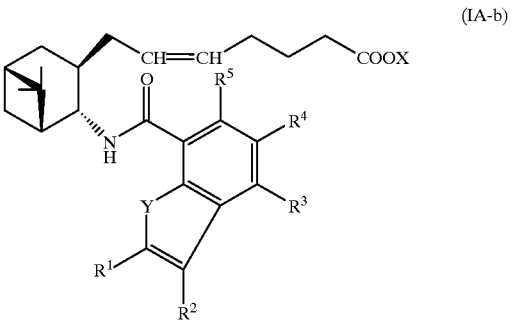

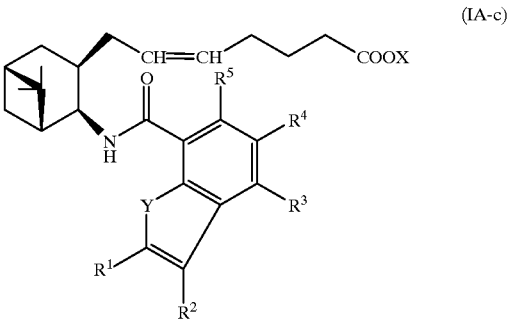

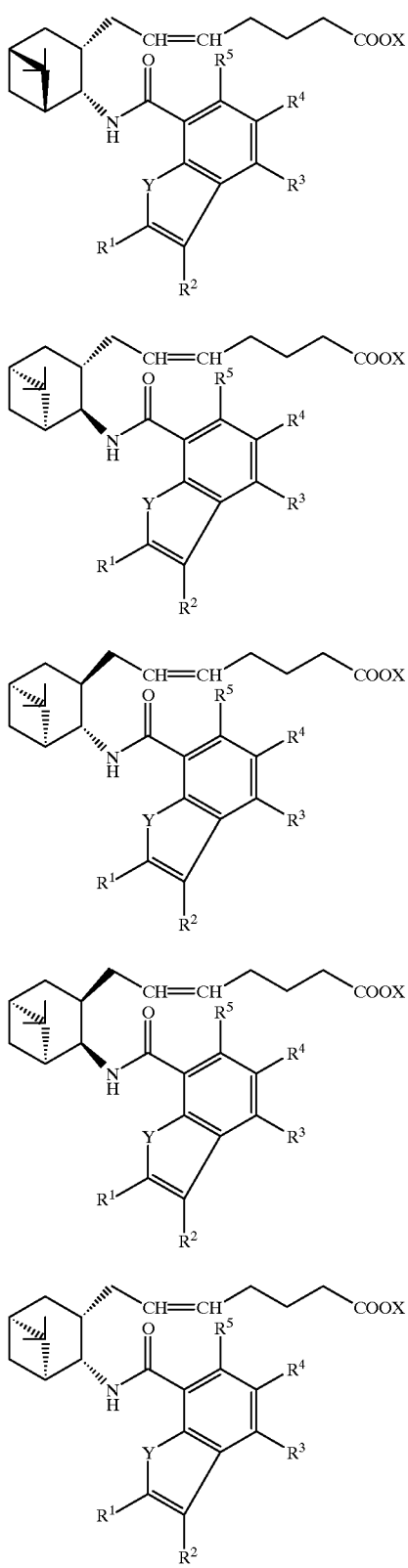
(IA-d)
(IA-a')
(IA-b')
(IA-c')
(IA-d')
wherein $R^1$, $R^2$, $R^3$, $R^4$, $R^5$, Y and X are as defined above, and the double bond on the α-chain has E configuration or Z configuration. Particularly, preferred examples of the compounds include those of the formula (IA-a).
Similarly, the compounds of the formula (IB) can be exemplified by:
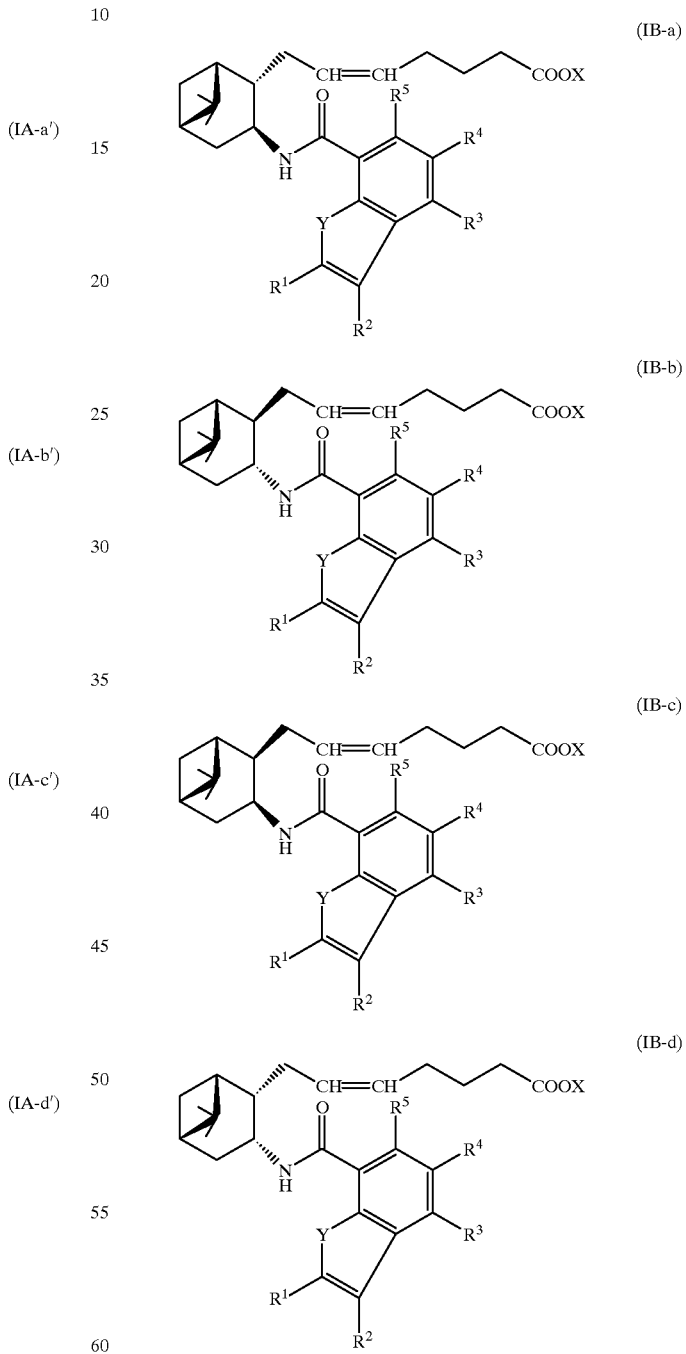
(IB-a)
(IB-b)
(IB-c)
(IB-d)

-continued

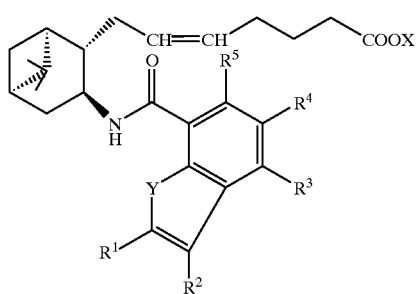
(IB-a′)

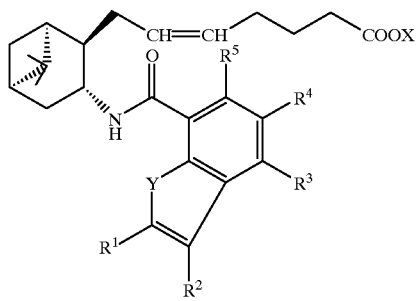
(IB-b′)

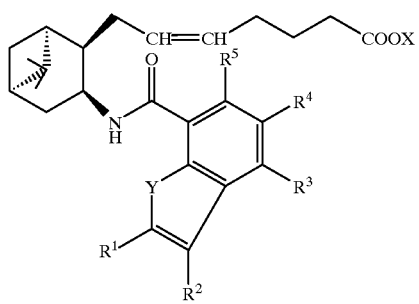
(IB-c′)

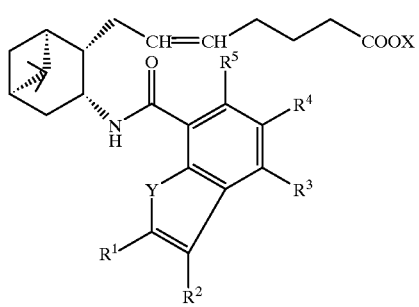
(IB-d′)

wherein $R^1$, $R^2$, $R^3$, $R^4$, $R^5$, Y and X are as defined above, and the double bond on the α-chain has E configuration or Z configuration.

In the compound of the formula (I), the group represented by the partial formula:

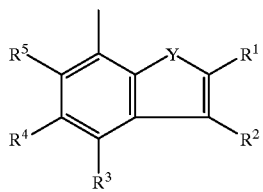

wherein $R^1$, $R^2$, $R^3$, $R^4$, $R^5$, and Y are as defined above;

can be exemplified by:

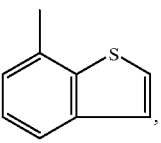 , 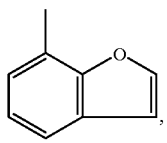 ,

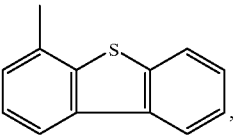 , 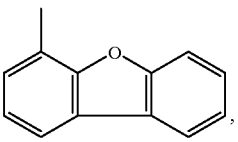 ,

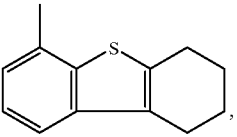 , 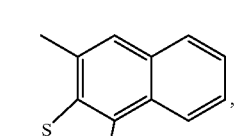 ,

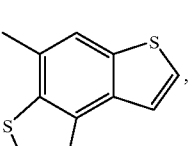 , 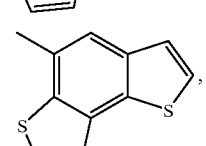 ,

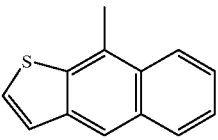

The ring may be substituted with alkyl, alkoxy, alkylthio, hydroxy, halogen, acyloxy, optionally substituted amino, or the like. Especially, the more preferable embodiment is the compound wherein $R^1$, $R^2$, $R^3$, $R^4$, and $R^5$ represent independently hydrogen, methyl, t-butyl, methylthio, methoxy, bromo, hydroxy, or acetoxy.

Especially, the more preferable embodiment is the compound of the formula (II):

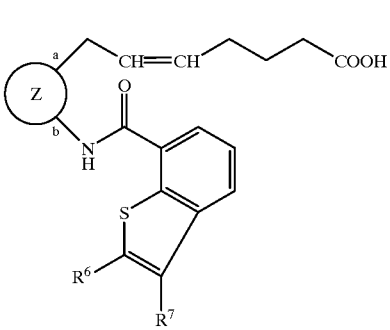
(II)

wherein

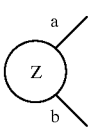

represents

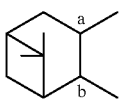 OR (A)

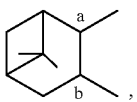 (B)

, $R^6$ and $R^7$ represent independently hydrogen, alkyl, alkoxy, alkylthio, hydroxy, halogen, or acyloxy, and the double bond on the α-chain has E configuration or Z configuration, pharmaceutically acceptable salt thereof, or hydrate thereof.

The more preferable embodiment of the compound (II) is the compound of the formule (IIA-a):

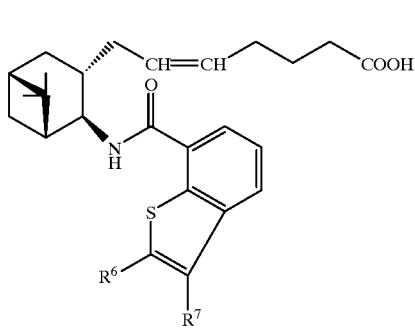 (IIA-a)

wherein $R^6$ and $R^7$ are as defined above, and the double bond on the α-chain has E configuration or Z configuration, pharmaceutically acceptable salt thereof, or hydrate thereof. Especially, the more preferable embodiment is the compound wherein $R^6$ and $R^7$ represent independently hydrogen, methyl, t-butyl, methylthio, methoxy, bromo, hydroxy, or acetoxy.

Especially, the most preferable embodiment is the compound of the formula (III):

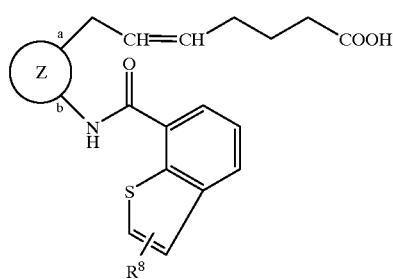 (III)

wherein

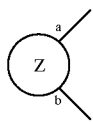

represents

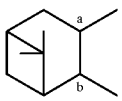 (A)

OR

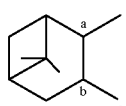 (B)

, $R^8$ represents hydrogen, alkyl, alkoxy, alkylthio, hydroxy, halogen, or acyloxy, and the double bond on the α-chain has E configuration or Z configuration, pharmaceutically acceptable salt thereof, or hydrate thereof.

The more preferable embodiment of the compound (III) is the compound of the formule (IIIA-a):

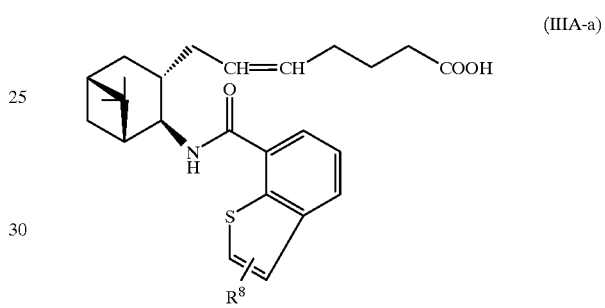 (IIIA-a)

wherein $R^8$ is as defined above, and the double bond on the α-chain has E configuration or Z configuration. Especially, the more preferable embodiment is the compound wherein $R^8$ represents hydrogen, methyl, t-butyl, methylthio, methoxy, bromo, hydroxy, or acetoxy.

Another embodiment of the present invention is the compound wherein the double bond on the α-chain has Z configuration, and the compound wherein the double bond on the α-chain has E configuration.

Another embodiment of the present invention is a pharmaceutical composition comprising the compound of the formula (I) or a $PGD_2$ antagonist comprising them. Particularly, the compounds of the formula (I) are useful as drugs for treating nasal blockage. $PGD_2$ antagonists in the present invention inhibit infiltration of inflammatory cells. The term "inflammatory cells" means all of lymphocytes, eosionophils, neutrophils, and macrophages, and particularly, eosionophils.

The compounds (I) in the present invention show $PGD_2$-antagonistic activities through the binding to $PGD_2$ receptor, so they are useful as drugs for treating diseases in which mast cell dysfunction caused by excessive production of $PGD_2$ is involved. For example, the compounds (I) are useful as drugs for treating diseases, such as systemic mastocytosis and disorder of systemic mast cell activation as well as tracheal contraction, asthma, allergic rhinitis, allergic conjunctivitis, urticaria, ischemic reperfusion injury, inflammation and atopic dermatitis. Moreover, the compounds (I) of the present invention possess an activity inhibiting infiltration of inflammatory cells. The compounds (I) are especially useful as drugs for treating nasal blockage.

The terms used throughout the present specification are as defined below.

The term "alkyl" means $C_1$–$C_8$ straight or branched chain alkyl, for example, methyl, ethyl, n-propyl, i-propyl, n-butyl, i-butyl, t-butyl, n-pentyl, i-pentyl, n-hexyl, n-heptyl, n-octyl and the like. Methyl is preferred.

The term "alkoxy" means $C_1$–$C_6$ alkoxy, for examples, methoxy, ethoxy, n-propoxy, i-propoxy, n-butoxy, and the like. Methoxyl is preferred.

The term "alkylthio" means alkylthio derived from the above-mentioned alkyl, for example, methylthio, ethylthio, propylthio, and the like. Methylthio is preferred.

The term "halogen" means fluoro, chloro, bromo and iodo.

The term "acyl" in the "acyloxy" means $C_1$–$C_9$ acyl derived from aliphatic carboxylic acids, for example, formyl, acetyl, propionyl, butyryl, valeryl, and the like. The term "acyloxy" means acyloxy derived from the above-mentioned acyl, for example, acetoxy, propionyloxy, butyryloxy, valeryloxy, and the like.

Substituents for the "optionally substituted amino" may be one or two substituent(s) selected from alkyl, acyl, alkoxycarbonyl, alkylsulfonyl, arylsulfonyl, and the like. The term "alkyl", "acyl", and "alkoxy" are as defined above. The term "aryl" means phenyl and naphthyl. Examples of "optionally substituted amino" includes, for example, methylamino, ethylamino, dimethylamino, acetylamino, methoxycarbonyl, ethoxycarbonyl, mesyl, ethylsulfonyl, benzenesulfonyl, toluenesulfonyl, and the like.

dimethylbenzylamine, 2-chlorobenzylamine, 4-methoxybenzylamine, 1-naphthalenemethylamine, diphenylbenzylamine, triphenylamine, 1-naphthylamine, 1-aminoanthracene, 2-aminoanthracene, dehydroabiethylamine, N-methylmorpholine or pyridine), an amino acid (e.g., lysine, or arginine), and the like.

Examples of hydrates of the compounds represented by the formula (I) may be coordinated with the compound (I) at the optional proportion.

The compounds represented by the formula (I) represent the optional steric configuration, the double bond on the α-chain has E configuration or Z configuration, the bond binding to the bicyclic ring represents R configuration or S configuration, and the compounds include the all isomers (diastereomers, epimers, enantiomers, and the like), racemates and mixtures thereof.

General processes for the preparation of the compounds of the present invention can be illustrated as follows. In the case of the compounds having substituents which interfere the reaction, such substituents may preliminarily be protected with protecting groups, and they may be removed in the suitable step.

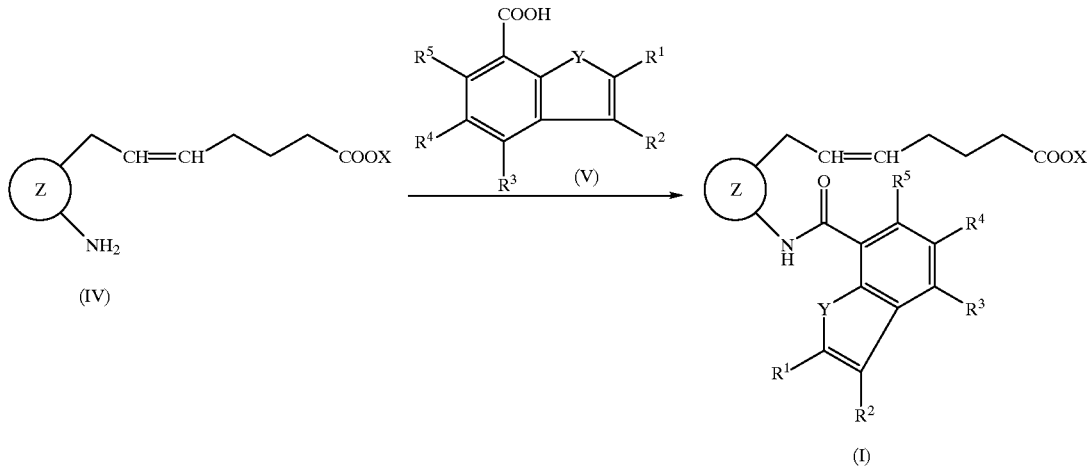

The term "carbon ring" means a saturated or unsaturated carbon ring, for example, a cyclo ring or a benzene ring.

The term "cyclo ring" means $C_3$–$C_8$ cycloalkyl, for example, cyclopropyl, cyclobutyl, cyclopentyl, cyclohexyl, cycloheptyl, and the like.

Substituents for the "optionally substituted carbon ring" and "optionally substituted thiophene" may be 1–3 substituent(s) selected from alkyl, alkoxy, alkylthio, hydroxy, halogen, acyloxy, and optionally substituted amino, and may be at any substitutable positions. The "alkyl", "alkoxy", "alkylthio", "hydroxy", "halogen", "acyloxy", and "optionally substituted amino" are as defined above.

Examples of salts of the compounds (I) include those formed with an alkali metal (e.g., lithium, sodium or potassium), an alkali earth metal (e.g., calcium), an organic base (e.g., tromethamine, trimethylamine, triethylamine, 2-aminobutane, t-butylamine, diisopropylethylamine, n-butylmethylamine, cyclohexylamine, dicyclohexylamine, N-isopropylcyclohexylamine, furfurylamine, benzylamine, methylbenzylamine, dibenzylamine, N,N- wherein the Z ring, $R^1$, $R^2$, $R^3$, $R^4$, $R^5$, Y and X are as defined above, and the double bond on the α-chain has E configuration or Z configuration.

The compounds of the formula (I) as shown in the above process can be prepared by reacting a carboxylic acid of the formula (V) or their reactive derivatives with an amino compounds of the formula (IV).

In this process, the starting compounds (IV)

wherein

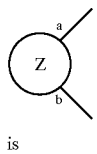

is

-continued

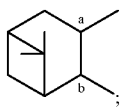
(A)

are described in the Japanese Patent Publication (Kokoku) No. 23170/1994.

The compounds wherein

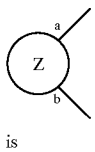

is

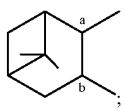
(B)

are described in the Japanese Patent Publication (Kokai) No. 49/1986 and 180862/1990.

The carboxylic acid of the formula (III) includes benzo[b]thiophene-7-carboxylic acid, 2-bromobenzo[b]thiophene-7-carboxylic acid, 3-bromobenzo[b]thiophene-7-carboxylic acid, 2,3-dibromobenzo[b]thiophene-7-carboxylic acid, 2-methylbenzo[b]thiophene-7-carboxylic acid, 3-methylbenzo[b]thiophene-7-carboxylic acid, 4-methylbenzo[b]thiophene-7-carboxylic acid, 5-methylbenzo[b]thiophene-7-carboxylic acid, 6-methylbenzo[b]thiophene-7-carboxylic acid, 2-methylthiobenzo[b]thiophene-7-carboxylic acid, 3-methylthiobenzo[b]thiophene-7-carboxylic acid, 2-methoxylbenzo[b]thiophene-7-carboxylic acid, 3-methoxylbenzo[b]thiophene-7-carboxylic acid, 4-methoxylbenzo[b]thiophene-7-carboxylic acid, 5-methoxylbenzo[b]thiophene-7-carboxylic acid, 6-methoxylbenzo[b]thiophene-7-carboxylic acid, 3-t-butylbenzo[b]thiophene-7-carboxylic acid, 3-hydroxylbenzo[b]thiophene-7-carboxylic acid, 4-hydroxylbenzo[b]thiophene-7-carboxylic acid, 5-hydroxylbenzo[b]thiophene-7-carboxylic acid, 6-hydroxylbenzo[b]thiophene-7-carboxylic acid, 2-acetoxylbenzo[b]thiophene-7-carboxylic acid, 3-acetoxylbenzo[b]thiophene-7-carboxylic acid, 6-acetoxylbenzo[b]thiophene-7-carboxylic acid, dibenzothiophene-4-carboxylic acid, naphtho[2,1-b]thiophene-4-carboxylic acid, 6-methoxynaphtho[2,1-b]thiophene-4-carboxylic acid, benzo[b]furan-7-carboxylic acid, dibenzofuran-4-carboxylic acid, and the like. These carboxylic acids can be substituted with the above defined substituents.

These carboxylic acids can be prepared in accordance with methods as described in J. Org. Chem., 3 108–119 (1938), J. Med. Chem., Vol.15, No.4, 370–373 (1972), J. Heterocyclic Chem., 25, 1271–1272 (1988), HETEROCYCLES. Vol.20, No.10, 2035–2037 (1983), J. Med. Chem. 38, 3951–3956(1995), J. Chem. Soc., 2624–2630(1957), J. Chem. Soc. Perkin Trans 11, 1479–1485(1984), and J. Org. Chem., 22, 687–689 (1957).

The reactive derivative of a carboxylic acid of the formula (V) means the corresponding acid halide (e.g., chloride, bromide, iodide), acid anhydride (e.g., mixed acid anhydride with formic acid or acetic acid), active ester (e.g., succinimide ester), and the like, and can generally be defined as acylating agents used for the acylation of amino group. For example, when an acid halide is employed, the compound (III) is reacted with a thionyl halide (e.g., thionyl chloride), phosphorous halide (e.g., phosphorous trichloride, phosphorous pentachloride), oxalyl halide (e.g., oxalyl chloride), and the like, in accordance with known methods as described in the literatures (e.g., Shin-Jikken-Kagaku-Koza, Vol. 14, 1787 (1978); Synthesis 852–854 (1986); Shin-Jikken-Kagaku-Koza Vol. 22, 115 (1992)).

The reaction can be conducted under a condition generally used for the acylation of amino group. For example, in the case of condensation with the acid halide, the reaction is carried out in a solvent such as an ether solvent (e.g., diethyl ether, tetrahydrofuran, dioxane), benzene solvent (e.g., benzene, toluene, xylene), halogenated solvent (e.g., dichloromethane, dichloroethane, chloroform) as well as ethyl acetate, dimethylformamide, dimethyl sulfoxide, acetonitrile, and those aqueous solvents, or the like, if necessary, in the presence of a base (e.g., organic base such as triethylamine, pyridine, N,N-dimethylaminopyridine, N-methylmorpholine; inorganic base such as sodium hydroxide, potassium hydroxide,potassium carbonate, or the like) under cooling at room temperature or under heating, preferably at a temperature ranging from −20° C. to ice-cooling temperature, or from room temperature to a refluxing temperature of the reaction system, for a period of several min to several hr, preferably for 0.5 hr to 24 hr, particularly, for 1 hr to 12 hr. In the case of using the carboxylic acid in a free form without converting into the reactive derivatives, the reaction is conducted in the presence of a condensing agent (e.g., dicyclohexylcarbodiimide (DCC), 1-ethyl-3-(3-dimethylaminopropyl)carbodiimide, N,N'-carbonyldiimidazole) usually used in the condensation reaction.

In the reaction of the other reactive derivatives or free acid with the amine (IV), according to the property of each reactive derivatives or free acid, in accordance with a known method, the reaction conditions are determined. The reaction product can be purified in accordance with a conventional purification, such as the extraction with a solvent, chromatography, recrystallization, and the like.

The objective compound (I) in the present invention can be converted into a corresponding ester derivative, if desired. For example, the ester can be prepared by esterification the carboxylic acid in accordance with a known method. If desired, E isomer, Z isomer or the mixtures can be produced depending on the reaction conditions.

When using a compound (I) of the present invention in treatment, it can be formulated into ordinary formulations for oral and parenteral administration. A pharmaceutical composition containing a compound (I) of the present invention can be in the form for oral and parenteral administration. Specifically, it can be formulated into formulations for oral administration such as tablets, capsules, granules, powders, syrup, and the like; those for parenteral administration such as injectable solution or suspension for intravenous, intramuscular or subcutaneous injection, inhalant, eye drops, nasal drops, suppositories, or percutaneous formulations such as ointment.

In preparing the formulations, carriers, excipients, solvents, and bases known to one ordinary skilled in the art may be used. In case of tablets, they are prepared by compressing or fomulating an active ingredient together with auxiliary components. Examples of usable auxiliary components include pharmaceutically acceptable excipients such as binders (e.g., cornstarch), fillers (e.g., lactose, microcrystalline cellulose), disintegrants (e.g., starch sodium glycolate) or lubricants (e.g., magnesium stearate). Tablets may be coated appropriately. In the case of liquid formulations such as syrups, solutions, or suspensions, they may contain suspending agents (e.g., methyl cellulose), emulsifiers (e.g., lecithin), preservatives and the like. In the case of injectable formulations, it may be in the form of solution or suspension, or oily or aqueous emulsion, which may contain suspension-stabilizing agent or dispensing agent, and the like. In the case of an inhalant, it is formulated into a liquid formulation applicable to an inhaler. In the case of eye drops, it is formulated into a solution or a suspension. Especially, in the case of nasal drug for treating nasal blockage, it can be used as a solution or suspension prepared by a conventional formulating method, or as a powder formulated using a powdering agent (e.g., hydroxypropyl cellulose, carbopole), which are administered into the nasal cavity. Alternatively, it can be used as an aerosol after filling into a special container together with a solvent of low boiling point.

Although an appropriate dosage of the compound (I) varies depending on the administration route, age, body weight, sex, or conditions of the patient, and the kind of drug(s) used together, if any, and should be determined by the physician in the end, in the case of oral administration, the daily dosage can generally be between about 0.01–100 mg, preferably about 0.01–10 mg, more preferably about 0.01 –1 mg, per kg body weight. In the case of parenteral administration, the daily dosage can generally be between about 0.001–100 mg, preferably about 0.001–1 mg, more preferably about 0.001–0.1 mg, per kg body weight. The daily dosage can be administered in 1–4 divisions.

The following Examples are provided to further illustrate the present invention and are not to be construed as limiting the scope.

The abbreviation used throughout the examples in the present invention are shown as follows.

| t-Bu | t-butyl |
| --- | --- |

REFERENCE EXAMPLE 1

Preparation of benzo[b]thiophene-7-carbonyl chloride (5)

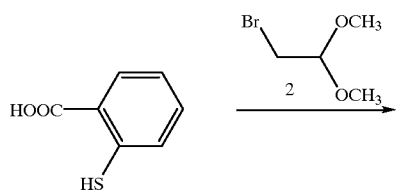

1

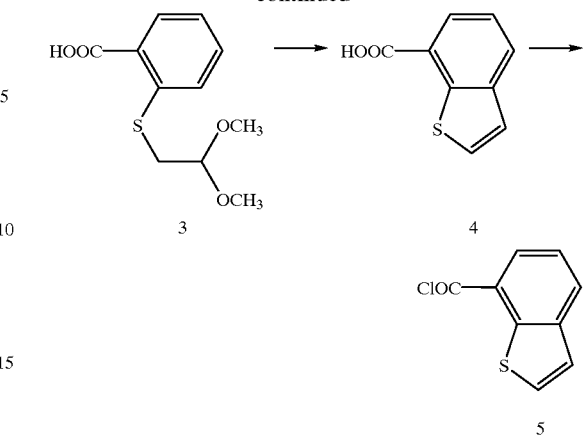

To methanol (77 ml) were added thio salicylic acid (1) (15.94 g, 103 mmol) and a 4.4 N solution of sodium methoxide (58.8 ml, 256 mmol). To the mixture was added 2-bromo-1,1-diethoxyethane (2) (14.7 ml, 131 mmol). The solution was refluxed for 2.5 hours. The reaction solution was diluted with iced water, and acidified with diluted hydrochloric acid. The precipitated crystals were filtered, washed, and dried to yield the compound (3) (23.87 g). Yield 95.3% mp 115–116° C.

To a refluxed solution of chlorobenzene (230 ml) and polyphosphoric acid (54 g) was added dropwise the compound (3) (23.87 g, 98.5 mmol) for 50 minutes. The mixture was refluxed for 2 hours, and then cooled down. The supernatant layer was removed by decantation, and the residue was washed with chlorobenzene. The supernatant layer and the washing solvent were collected, and concentrated under reduced pressure. The obtained red residue was dissolved in a 10% sodium hydroxide solution (40 ml), and washed with toluene (40 ml). The aqueous layer was neutralized with 10% hydrochloric acid. The precipitated crystals were filtered, washed, and recrystallized from alcohol to yield the carboxylic acid (4) (12.11 g).

Yield 68.9% mp 186–187° C.

The toluene solution (3 ml) of the compound (4) (231 mg, 1.3 mmol), thionyl chloride (0.28 ml), and dimethylformamide (1 drop) was refluxed for 1 hour. The solvent was concentrated under reduced pressure to yield the objective compound (5) 236 mg. Yield 100%

EXAMPLE 1

Preparation of sodium (5Z)-7-{(1R, 2R, 3S, 5S)-2-(benzo[b]thiophene-7yl-carbonylamino-6, 6-dimethyl-bicyclo[3. 1. 1]hept-3-yl}-5-heptenoate (IA-a-2)

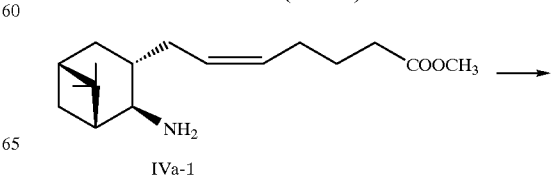

IVa-1

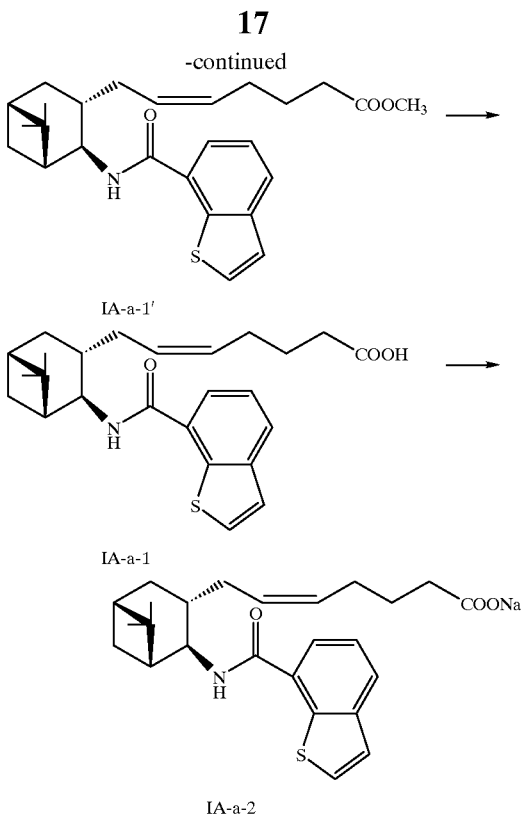

(Step 3)

In methanol (16 ml) was dissolved the compound (IA-a-1) (1,00 g, 2.35 mmol). To the solution was added 1 N sodium hydroxide (2.23 ml, 2.23 mmol). The solvent was concentrated under reduced pressure. The residue was dissolved with ethyl acetate, and diluted with n-hexane. The indissolved substance was dissolved in methanol, concentrated under reduced pressure, and dried to yield the objective (IA-a-2) (1.053 g). Yield 100%

$[\alpha]_D^{23}=+51.7°$ ($c$=1.01%, $CH_3OH$)

Elementary Analysis (for $C_{25}H_{30}NO_3SNa \cdot 0.3H_2O$)

Calcd (%): C, 66.29; H, 6.67; N, 3.09; S, 7.08; Na, 5.08
Found (%): C, 66.04; H, 6.92; N, 3.24; S, 6.97; Na, 4.81

Compounds and physical constants obtained in the same manner as the above Examples are shown in the following table 1 – table 10.

(Step 1)

In tetrahydrofuran (3 ml) was dissolved the compound (IVa-1) (279 mg, 1.0 mmol) described in Japanese Patent Publication (Kokoku) No. 231701/1994. To the solution were added triethylamine (0.5 ml, 3.6 mmol) and benzo[b]thiophene-7-carbonyl chloride (5) (236 mg, 1.2 mmol) described in Reference Example 1. The mixture was refluxed for 2 hours, diluted with water, and extracted with toluene. The organic layer was washed with diluted hydrochloride and water, dried over anhydrous magnesium sulfate, and concentrated under reduced pressure. The residue was chromatographed on silica gel (toluene:ethyl acetate 96:4) to yield the compound (IA-a-1') 433 mg. Yield 98.5%

$[\alpha]_D^{23}=+63.1°$ ($c$=1.01%, $CH_3OH$)

Elementary Analysis (for $C_{26}H_{33}NO_3S \cdot 0.1H_2O$)

Calcd (%): C, 70.75; H, 7.58; N, 3.17; S, 7.26
Found (%): C, 70.58; H, 7.75; N, 3.30; S, 7.34

(Step 2)

In methanol (4 ml) was dissolved the compound (IA-a-1') (433 mg, 0.99 mmol). To the solution was added 4 N sodium hydroxide (0.61 ml, 2.46 mmol). The solution was stirred for 6 hours, neutralized with 1 N hydrochloric acid (2.5 ml), diluted with water, and extracted with ethyl acetate. The organic layer was washed with water, dried over anhydrous magnesium sulfate, and concentrated under reduced pressure. The residue was crystallized from toluene / n-hexane to yield the objective (1A-a-1) (376 mg) as a prism crystal. Yield 89.3%
mp 85–87° C.

$[\alpha]_D^{23}=+68.5°$ ($c$=1.01%, $CH_3OH$)

Elementary Analysis (for $C_{25}H_{31}NO_3S$)

Calcd (%): C, 70.56; H, 7.34; N, 3.29; S, 7.53
Found (%): C, 70.47; H, 7.43; N, 3.54; S, 7.53

TABLE 1

| Compd No. | X | R |
|---|---|---|
| IA-a-1 | H | 7-benzo[b]thiophenyl |
| IA-a-1' | $CH_3$ | 7-benzo[b]thiophenyl |
| IA-a-2 | Na | 7-benzo[b]thiophenyl |
| IA-a-3 | H | 2,3-dibromo-7-benzo[b]thiophenyl |
| IA-a-4 | H | 3-methyl-7-benzo[b]thiophenyl |

TABLE 1-continued

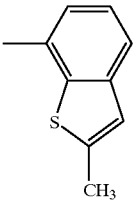

| Compd No. | X | R |
|---|---|---|
| IA-a-5 | H | 7-methyl-2-methylbenzothiophene |
| IA-a-6 | H | 7-methyl-2-(methylthio)benzothiophene |
| IA-a-7 | H | 7-methyl-3-bromobenzothiophene |
| IA-a-8 | H | 7-methyl-2-bromobenzothiophene |
| IA-a-9 | H | 7-methyl-3-methoxybenzothiophene |
| IA-a-10 | H | 7-methyl-3-t-butylbenzothiophene |

TABLE 1-continued

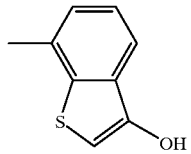

| Compd No. | X | R |
|---|---|---|
| IA-a-11 | H | 4-methyldibenzothiophene |
| IA-a-12 | H | 4-methylnaphtho[thiophene] |
| IA-a-13 | H | 4-methyl-6-methoxynaphtho[thiophene] |
| IA-a-14 | H | 4-methyldibenzofuran |

TABLE 2

| Compd No. | R |
|---|---|
| IA-a-15 | 7-methyl-3-hydroxybenzothiophene |

TABLE 2-continued

| Compd No. | R |
|---|---|
| IA-a-16 | 6-hydroxy-7-methylbenzo[b]thiophene |
| IA-a-17 | 5-hydroxy-7-methylbenzo[b]thiophene |
| IA-a-18 | 4-hydroxy-7-methylbenzo[b]thiophene |
| IA-a-19 | 6,7-dimethylbenzo[b]thiophene |
| IA-a-20 | 5,7-dimethylbenzo[b]thiophene |
| IA-a-21 | 4,7-dimethylbenzo[b]thiophene |
| IA-a-22 | 7-methyl-3-(methylthio)benzo[b]thiophene |

TABLE 2-continued

| Compd No. | R |
|---|---|
| IA-a-23 | 6-methoxy-7-methylbenzo[b]thiophene |
| IAa-24 | 5-methoxy-7-methylbenzo[b]thiophene |
| IA-a-25 | 4-methoxy-7-methylbenzo[b]thiophene |
| IA-a-26 | 2-methoxy-7-methylbenzo[b]thiophene |
| IA-a-27 | 2-acetoxy-7-methylbenzo[b]thiophene |
| IA-a-28 | 3-acetoxy-7-methylbenzo[b]thiophene |

TABLE 2-continued
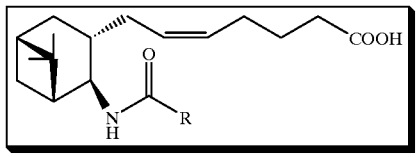
| Compd No. | R |
|---|---|
| IA-a-29 | 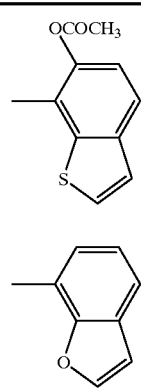 |
| IA-a-30 | 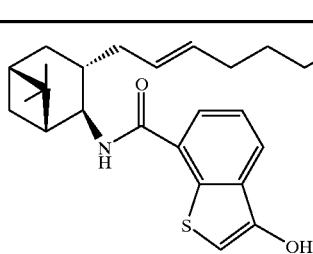 |
TABLE 3
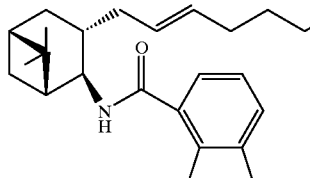
| Compd No. | |
|---|---|
| IA-a-31 | 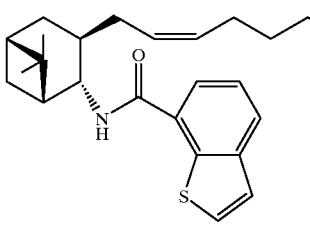 |
| IA-a-32 | 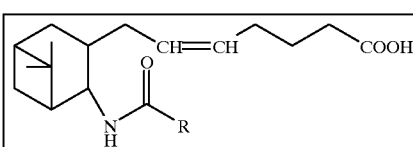 |
| IA-b-1 | 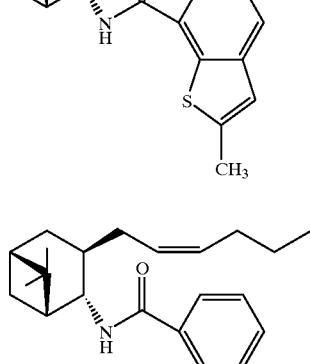 |
TABLE 3-continued
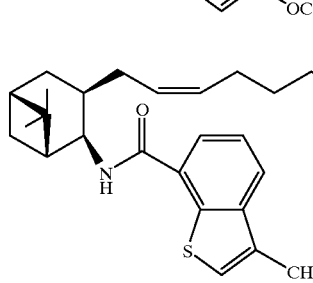
| Compd No. | |
|---|---|
| IA-b-2 | 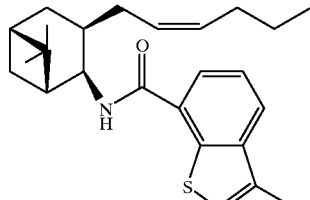 |
| IA-b-3 | 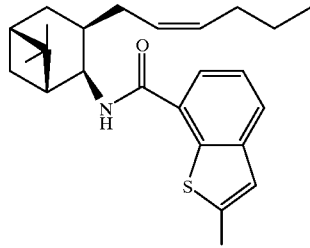 |
| IA-c-1 | |
| IA-c-2 | |
| IA-c-3 | |

TABLE 3-continued
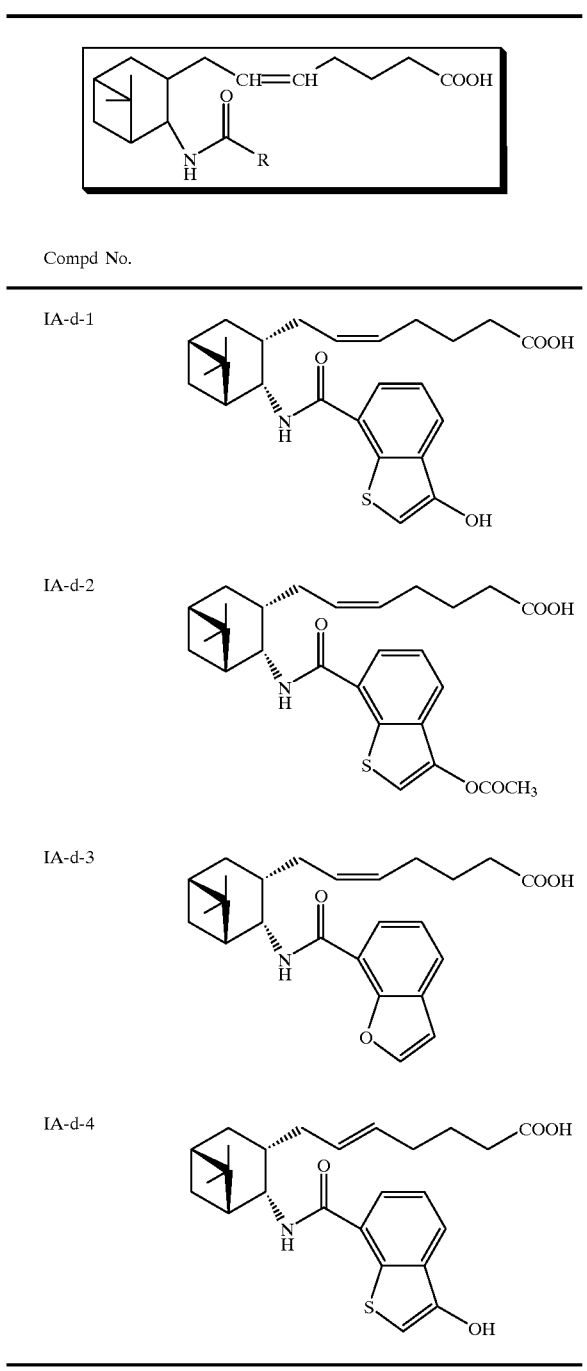
TABLE 4
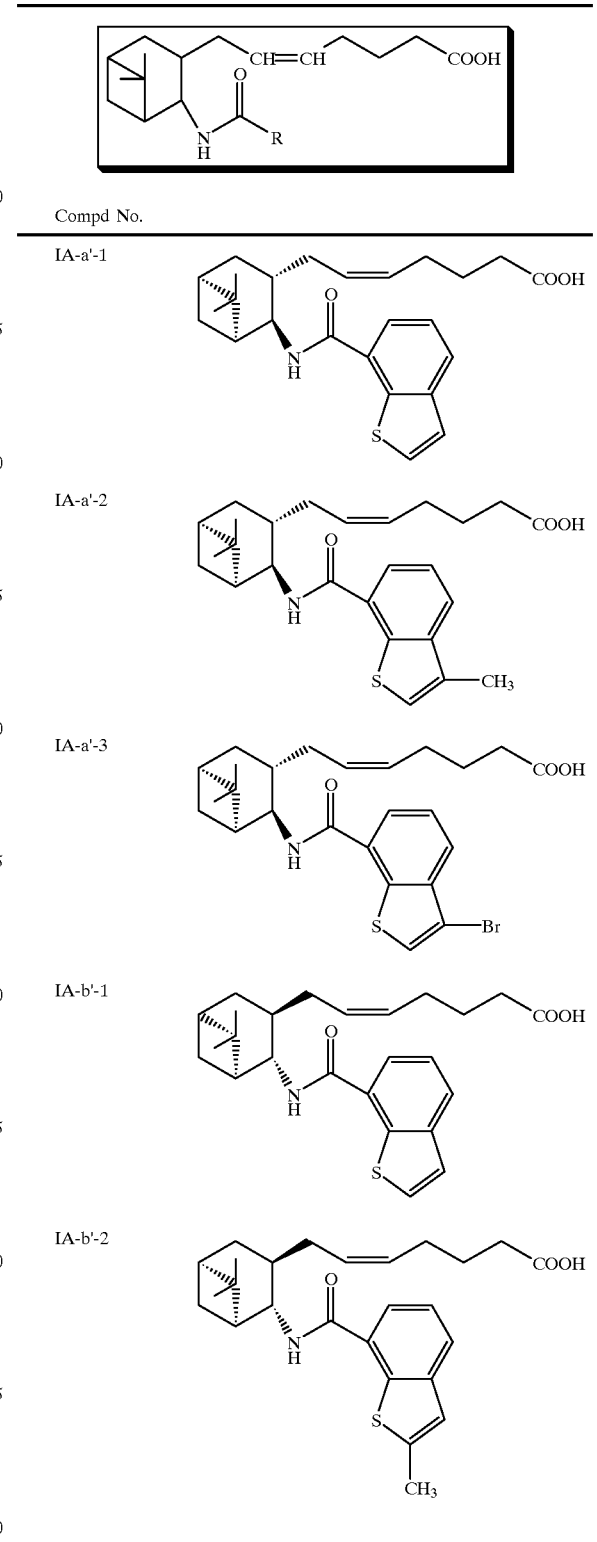

TABLE 4-continued
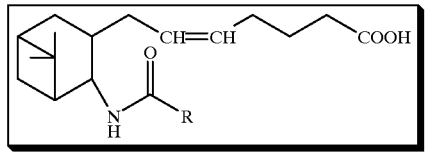
| Compd No. | |
|---|---|
| IA-b'-3 | 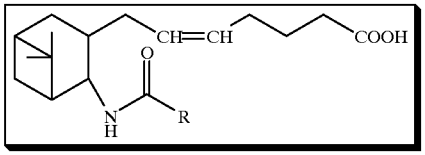 |
| IA-c'-1 | 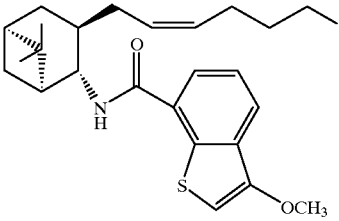 |
| IA-c'-2 | 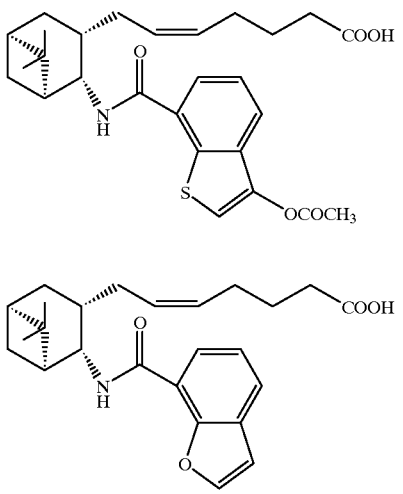 |
| IA-c'-3 | 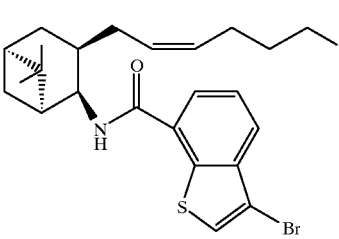 |
| IA-d'-1 | 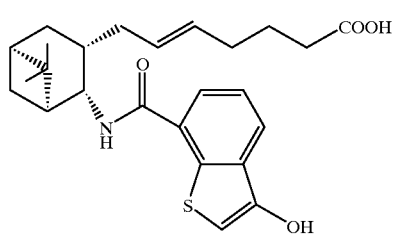 |
TABLE 4-continued
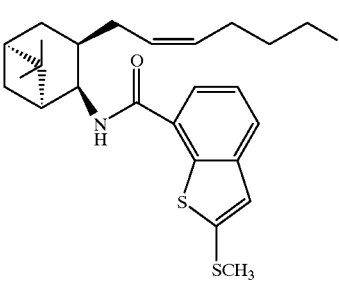
| Compd No. | |
|---|---|
| IA-d'-2 | 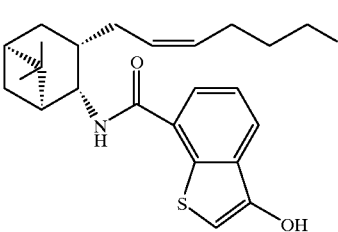 |
| IA-d'-3 | 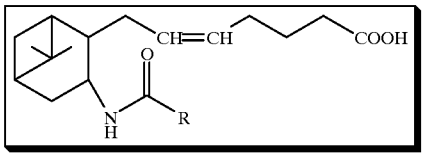 |
| IA-d'-4 | 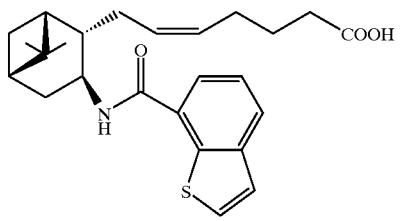 |
TABLE 5
| Compd No. | |
|---|---|
| IB-a-1 | |

TABLE 5-continued
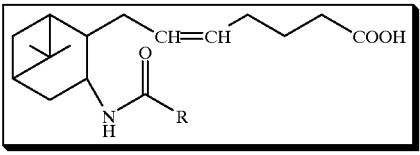
| Compd No. | |
|---|---|
| IB-a-2 | 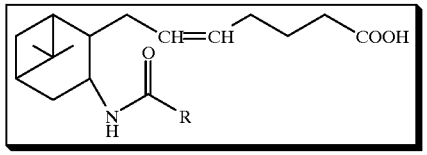 |
| IB-a-3 | 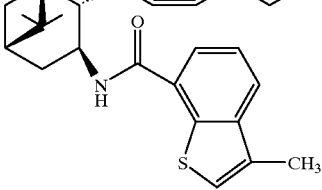 |
| IB-b-1 | 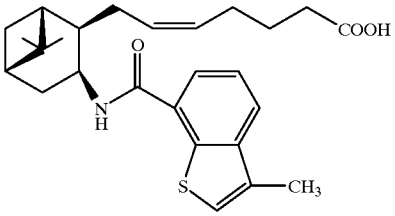 |
| IB-b-2 | 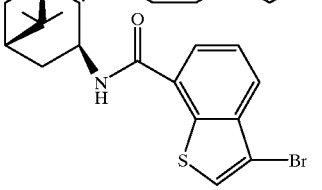 |
| IB-b-3 | 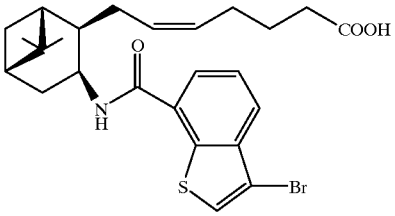 |
| IB-c-1 | 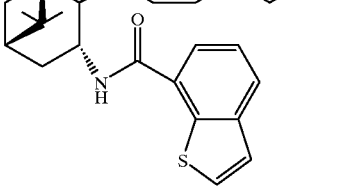 |
| IB-c-2 | 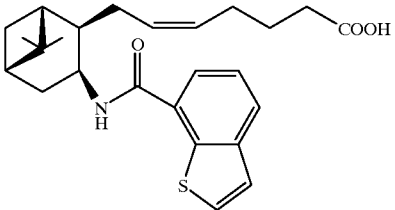 |
| IB-c-3 | 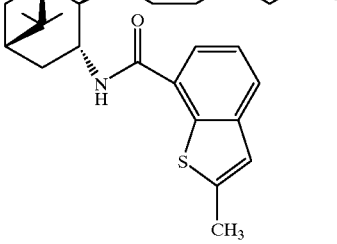 |
| IB-d-1 | 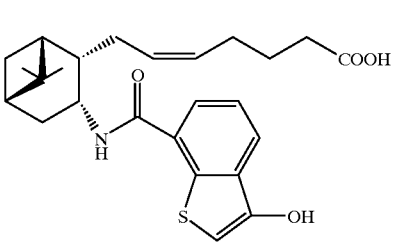 |
| IB-d-2 | 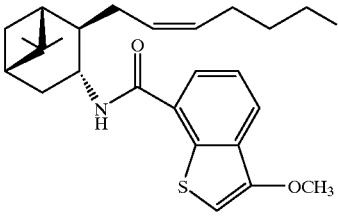 |

TABLE 5-continued
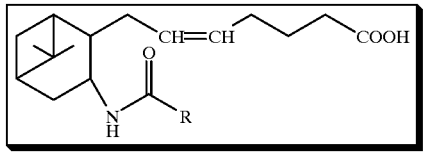
| Compd No. | |
|---|---|
| IB-d-3 | 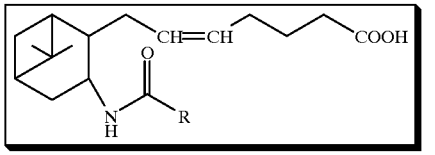 |
| IB-d-4 | 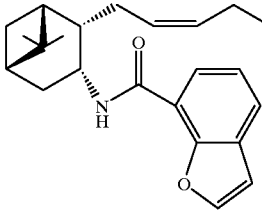 |
TABLE 6
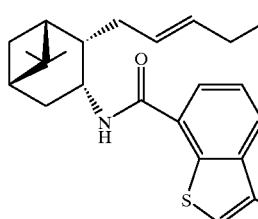
| Compd. No. | |
|---|---|
| IN-a'-1 | 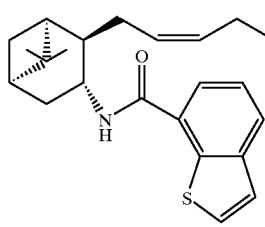 |
| IB-a'-2 | 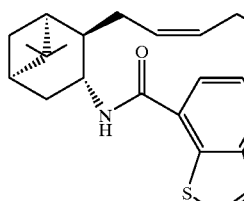 |
TABLE 6-continued
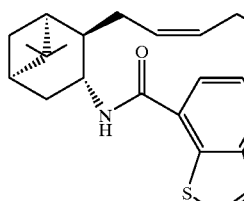
| Compd. No. | |
|---|---|
| IB-a'-3 | 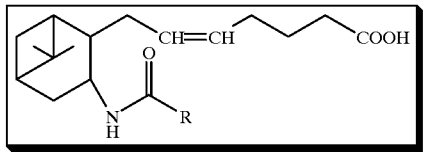 |
| IB-b'-1 | 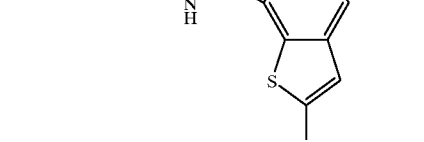 |
| IB-b'-2 | 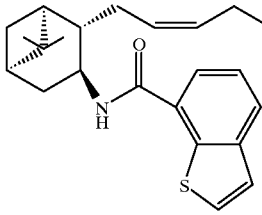 |
| IB-b'-3 | 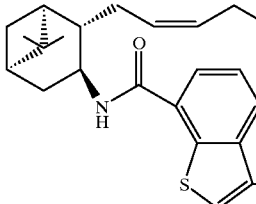 |
| IB-c'-1 | 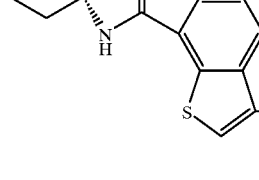 |

TABLE 6-continued

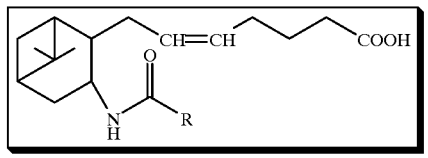

| Compd. No. | |
|---|---|
| IB-c'-2 | 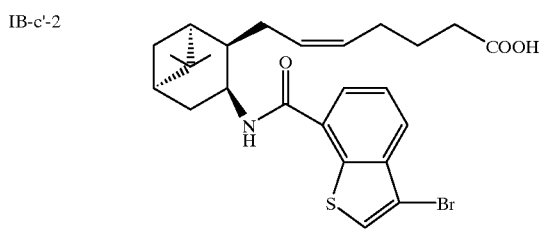 |
| IB-c'-3 | 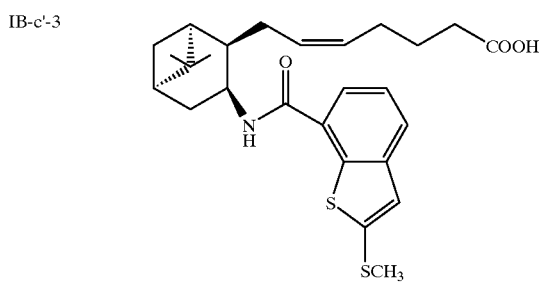 |
| IB-d'-1 | 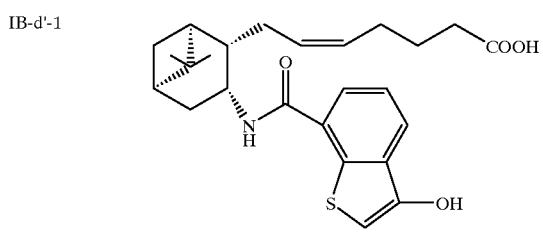 |

TABLE 6-continued

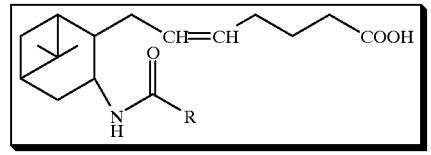

| Compd. No. | |
|---|---|
| IB-d'-2 | 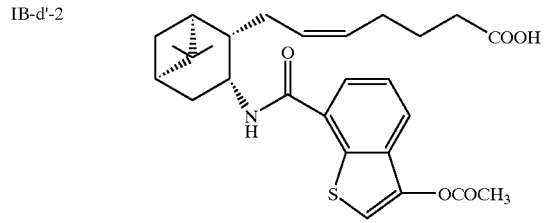 |
| IB-d'-3 | 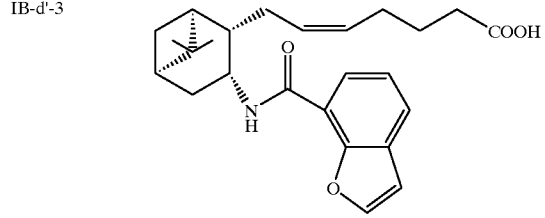 |
| IB-d'-4 | 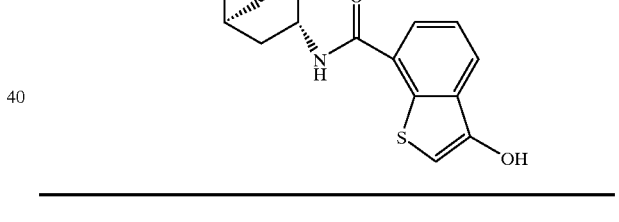 |

TABLE 7

| Compd. No. | Physical constant |
|---|---|
| IA-a-1 | NMR δ (CDCl$_3$ ppm), 300MHz<br>0.99 (1H, d, J=10.2Hz), 1.16 and 1.24 (each 3H, each s), 1.54–2.52 (14H, m), 4.40 (1H, m), 5.34–5.53 (2H ,m), 6.49 (1H, d, J=9.0Hz), 7.38 and 7.58 (each 1H, d, J=5.7Hz), 7.42 (1H, t, J=7.7Hz), 7.55 (1H, m), 7.59 (1H, m).<br>IR (CHCl$_3$): 3517, 3457, 3419, 3063, 3028, 3013, 2925, 2870, 2669, 1740, 1708, 1650, 1584, 1567, 1519, 1495 cm$^{-1}$. |
| IA-a-2 | (CD$_3$OD) 0.99 (1H, d, J=9.6Hz), 1.18 and 1.24 (each 3H, each s), 1.54–2.46 (14H, m), 4.24 (1H, in), 5.39–5.51 (2H, m), 7.41 and 7.65 (each 1H, d, J=5.7Hz), 7.45 (1H, t, J=7.8Hz), 7.80 (1H, m), 7.99(1H, m).<br>IR (KBr): 3512, 3062, 2984, 2921, 2867, 1636, 1567, 1523, 1496, 1459 cm$^{-1}$.<br>[α]$_D$ +51.6° (CH$_3$OH, c = 1.00, 26° C). |
| IA-a-3 | 0.99 (1H, d, J=9.9Hz), 1.16 and 1.24 (each 3H, each s), 1.54–2.49 (14H, m), 4.37 (1H, m), 5.34–5.51 (2H, m), 6.49 (1H, d, J=8.7Hz), 7.47 (1H, t, J=7.5Hz), 7.52 (1H, dd, J=1.5 and 7.5Hz), 7.88 (1H, dd, 1.5 and |

TABLE 7-continued

| Compd. No. | Physical constant |
|---|---|
| | 7.5Hz).<br>IR(CHCl$_3$): 3517, 3457, 3419, 3063, 3028, 3013, 2925, 2870, 2669, 1740, 1708, 1650, 1584, 1567, 1519, 1495 cm$^{-1}$.<br>[α]$_D$ +48.10 (CH$_3$OH, c = 1.01, 26° C). |
| IA-a-4 | 0.99 (1H, d, J=9.9Hz), 1.15 and 1.24 (each 3H, each s), 1.54–2.52 (14H, m), 2.45 (3H, d, J=1.2Hz), 4.40 (1H, m), 5.34–5.53 (2H, m), 6.49 (1H, d, J=9.0Hz), 7.21 (1H, m), 7.44 (1H, t, J=7.8Hz), 7.54 (1H, m), 7.84 (1H, dd, J=0.9 and 7.8Hz).<br>IR(CHCl$_3$): 3511, 3456, 3416, 2663, 1708, 1650, 1507 cm$^{-1}$.<br>[α]$_D$ +65.9° (CH$_3$OH, c = 1.01, 25° C.). |

TABLE 8

| Compd. No. | Physical constant |
|---|---|
| IA-a-5 | 0.99 (1H, d, J=9.9Hz), 1.15 and 1.23 (each 3H, each s), 1.54–2.51 (14H, m), 2.60 (3H, d, J=1.2Hz), 4.38 (1H, m), 5.34–5.53 (2H, m), 6.46 (1H, d, J=8.4Hz), 7.01 (1H, m), 7.35 (1H, t, J=7.8Hz), 7.45 (1H, dd, J=0.9 and 7.8Hz), 7.77 (1H, dd, J=0.9 and 7.8Hz).<br>IR(CHCl$_3$): 3517, 3456, 3418, 2662, 1740, 1707, 1650, 1508 cm$^{-1}$.<br>[α]$_D$ +57.0° (CH$_3$OH, c = 1.01, 25° C.). |
| IA-a-6 | 0.99 (1H, d, J=10.2Hz), 1.15 and 1.23 (each 3H, each s), 1.54–2.51 (14H, m), 2.63 (3H, s), 4.38 (1H, m), 5.34–5.52 (2H, m), 6.46 (1H, d, J=8.4Hz), 7.18 (1H, s), 7.36 (1H, t, J=7.8Hz), 7.42 (1H, dd, J=1.2 and 7.5Hz), 7.76 (1H, dd, J=1.2 and 7.5Hz).<br>IR(CHCl$_3$): 3512, 3457, 2667, 1741, 1708, 1649, 1519, 1494 cm$^{-1}$.<br>[α]$_D$ +45.3° (CH$_3$OH, c = 1.01, 25° C.). |
| IA-a-7 | 0.99 (1H, d, J=10.2Hz), 1.16 and 1.24 (each 3H, each s), 1.54–2.51 (14H, m), 4.39 (1H, m), 5.34–5.52 (2H, m), 6.48 (1H, d, J=8.4Hz), 7.52 (1H, t, J=7.8Hz), 7.59 (1H, dd, J=1.2 and 7.8Hz), 7.59 (1H, s), 7.98 (1H, dd, J=1.2 and 7.8Hz).<br>IR(CHCl$_3$): 3517, 3456, 2666, 1708, 1650, 1517, 1493 cm$^{-1}$.<br>[α]$_D$ +65.4° (CH$_3$OH, c = 1.01, 23° C.). |
| IA-a-8 | 0.99 (1H, d, J=10.2Hz), 1.16 and 1.24 (each 3H, each s), 1.54–2.50 (14H, m), 4.37 (1H, m), 5.34–5.51 (2H, m), 6.47 (1H, d, J=8.7Hz), 7.36 (1H, s), 7.38 (1H, t, J=7.8Hz), 7.46 (1H, dd, J=1.2 and 7.8Hz), 7.82 (1H, dd, J=1.2 and 7.8Hz).<br>IR(CHCl$_3$): 3516, 3458, 2667, 1708, 1649, 1522, 1498 cm$^{-1}$.<br>[α]$_D$ +45.0° (CH3OH, c = 1.01, 23° C.). |

TABLE 9

| Compd. No. | Physical constant |
|---|---|
| IA-a-9 | 0.99 (1H, d, J=10.2Hz), 1.16 and 1.24 (each 3H, each s), 1.55–2.52 (14H, m), 3.98 (3H, s), 4.38 (1H, m), 5.34–5.53 (2H, m), 6.42 (1H, s), 6.49 (1H, d, J=8.4Hz), 7.41 (1H, t, J=7.8Hz), 7.58 (1H, dd, J=0.9 and 7.8Hz), 7.93 (1H, dd, J=0.9 and 7.8Hz).<br>IR(CHCl$_3$): 3511, 3457, 3413, 2663, 1741, 1708, 1650, 1508 cm$^{-1}$.<br>[α]$_D$ +60.4° (CH3OH, c = 1.01, 24° C.). |
| IA-a-10 | 0.99 (1H, d, J=10.2Hz), 1.16 and 1.24 (each 3H, each s), 1.47 (9H, s), 1.54–2.52 (14H, m), 4.38(1H, m), 5.34–5.53 (2H, m), 6.48 (1H, d, J=8.7Hz), 7.07 (1H, s), 7.35 (1H, t, J=7.8Hz), 7.45 (1H, dd, J=1.2 and 7.8Hz).<br>IR(CHCl$_3$): 3516, 3457, 3417, 2668, 1740, 1708, 1648, 1506 cm$^{-1}$.<br>[α]$_D$ +54.8° (CH$_3$OH, c = 1.01, 25° C.). |
| IA-a-11 | 1.01 (1H, d, J=9.9Hz), 1.17 and 1.25 (each 3H, each s), 1.55–2.54 (14H, m), 4.42 (1H, m), 5.35–5.54 (2H, m), 6.52 (1H, d, J=8.7Hz), 7.43–7.49 (2H, m), 7.53 (1H, d, J=7.8Hz), 7.66 (1H, dd, J=0.9 and 7.5Hz), 7.91 (1H, m), 8.16 (1H, m), 8.29 (1H, dd, J=1.2 and 7.8Hz).<br>IR(CHCl$_3$): 3515, 3457, 2666, 1741, 1708, 1650, 1510, 1471 cm$^{-1}$.<br>[α]$_D$ +65.3° (CH$_3$OH, c = 1.01, 25° C.). |
| IA-a-12 | 1.02 (1H, d, J=10.2Hz), 1.20 and 1.26 (each 3H, each s), 1.57–2.54 (14H, m), 4.43 (1H, m), 5.35–5.56 (2H, m), 6.60 (1H, d, J=9.0Hz), 7.57 (1H, m), 7.68 (1H, m), 7.73 (1H, d, J=5.7Hz), 7.96 (1H, s), 7.99 (1H, m), 8.01 (1H, d, J=5.4Hz), 8.36 (1H, m).<br>IR(CHCl$_3$): 3671, 3514, 3451, 2669, 1739, 1708, 1649, 1515 cm$^{-1}$.<br>[α]$_D$ +72.8° (CH$_3$OH, c = 1.00, 25° C.). |

TABLE 10

| Compd. No. | Physical constant |
|---|---|
| IA-a-13 | 1.01 (1H, d, J=9.9Hz), 1.22 and 1.25 (each 3H, each s), 1.57–2.56 (14H, m), 4.07 (3H, s), 4.41 (1H, m), 5.35–5.58 (2H, m), 6.81 (1H, d, J=8.4Hz), 6.95 (1H, d, J=7.2Hz), 7.59 (1H, t, J=8.1Hz), 7.72 (1H, d, J=5.7Hz), 7.94 (1H, m), 7.97 (1H, d, J=5.7Hz), 8.49 (1H, s). IR(CHCl$_3$): 3513, 2667, 1647, 1620, 1515, 1493, 1461 cm$^{-1}$. [α]$_D$ +73.2° (CH$_3$OH, c = 1.00, 25° C.). |
| IA-a-14 | 1.04 (1H, d, J=10.5Hz), 1.28 and 1.37 (each 3H, each s), 1.57–2.58 (14H, m), 4.50 (1H, m), 5.34–5.56 (2H, m), 7.36–7.56 (4H, m), 7.96 (1H, dd, J=1.5 and 7.5Hz), 8.05 (1H, dd, J=1.5 and 7.5Hz), 8.09 (1H, d, J=9.0Hz), 8.27 (1H, dd, J=1.5 and 7.5Hz). IR(CHCl$_3$): 3517, 2670, 1738, 1708, 1655, 1537, 1490, 1473 cm$^{-1}$. [α]$_D$ +42.2° (CH$_3$OH, c = 1.00, 24° C.). |

The compounds prepared in Examples above were tested for determining the in vivo and in vitro activities according to the method as shown in Experimental examples below.

Experiment 1 Binding to PGD$_2$ Receptor

Materials and Methods (1) Preparation of Human Platelet Membrane Fraction

Blood sample was obtained using a plastic syringe containing 3.8% sodium citrate from the vein of healthy volunteers (adult male and female), put into a plastic test tube and mixed gently by rotation. The sample was then centrifuged at 1800 rpm, 10 min at room temperature, and the supernatant containing PRP (platelet-rich plasma) was collected. The PRP was re-centrifuged at 2:300 rpm, 22 min at room temperature to obtain platelets. The platelets were homogenized using a homogenizer (Ultra-Turrax) followed by centrifugation 3 times at 20,000 rpm, 10 min at 4° C. to obtain a platelet membrane fraction. After protein determination, the membrane fraction was adjusted to 2 mg/ml and preserved in a refrigerator at −80° C. until use.

(2) Binding to PGD$_2$ Receptor

To a binding-reaction solution (50 mM Tris/HCl, pH 7.4, 5 mM MgCl$_2$) (0.2 ml) were added the human platelet membrane fraction (0.1 mg) and 5 nM [$^3$H]PGD$_2$ (115Ci/mmol), and reacted at 4° C. for 90 min. After the reaction completed, the reaction mixture was filtered through a glass fiber filter paper, washed several times with cooled saline, and measured the radioactivity retained on the filter paper. The specific binding was calculated by subtracting the non-specific binding (the binding in the presence of 10 μM PGD$_2$) from the total binding. The inhibitory activity of each compound was expressed as the concentration required for 50% inhibition (IC$_{50}$), which was determined by depicting a substitution curve by plotting the binding ratio (%) in the presence of each compound, where the binding ratio in the absence of a test compound is 100%. The results are shown in Table 11.

TABLE 11

| Compd. No. | IC$_{50}$ (nM) |
|---|---|
| IA-a-1 | 26 |
| IA-a-4 | 11 |
| IA-a-7 | 1.2 |
| IA-a-9 | 0.41 |

Experiment 2 Evaluation of Antagonistic Activity Against PGD$_2$ Receptor Using Human Platelet Peripheral blood was obtained from a healthy volunteer using a syringe in which ⅑ volume of citric acid/dextrose solution has been previously added. The syringe was subjected to centrifugation at 180 g for 10 min to obtain the supernatant (PRP:platelet rich plasma). The resultant PRP was washed 3 times with a washing buffer and the number of platelet was counted with a micro cell counter. A suspension adjusted to contain platelet at a final concentration of 5×10$^8$/ml was warmed at 37° C., and then subjected to the pre-treatment with 3-isobutyl-1-methylxanthine (0.5 mM) for 5 min. To the suspension was added a test compound diluted at various concentration. Ten-minute later, the reaction was induced by the addition of 0.1 μM PGD$_2$ and, 2-minute later, stopped by the addition of hydrochloric acid. The platelet was destroyed with an ultrasonic homogenizer. After centrifugation, the cAMP in the supernatant was determined by radioimmunoassay. PGD$_2$ receptor antagonism of a drug was evaluated as follows. The inhibition rate regarding cAMP increased by the addition of PGD$_2$ was determined at individual concentration, and then the concentration of the drug required for 50% inhibition (IC$_{50}$) was calculated. The results are shown in Table 12.

TABLE 12

| Compd. No. | IC$_{50}$ (nM) |
|---|---|
| IA-a-1 | 42 |
| IA-a-4 | 150 |
| IA-a-7 | 11 |
| IA-a-9 | 4.4 |

Experiment 3 Experiment Using Nasal Blockage Model

The method used for measuring the intranasal pressure for evaluating the anti-nasal blockage using guinea pigs is described below.

A 1% ovalbumin (OVA) solution was treated with an ultrasonic nebulizer to obtain an aerosol. Hartley male guinea pig was sensitized by inhaling twice the aerosol for 10 min at one-week interval. Seven-day after the sensitization, the guinea pig was exposed to an antigen to initiate the reaction. Briefly, the trachea was incised under the anesthesia with pentobarbital (30 mg/kg. i.p.) and cannulas were inserted into the trachea at the pulmonary and nasal cavity sides. The canal inserted at the pulmonary side was connected with an artificial respirator that provides 4 ml air 60 times/min. After arresting the spontaneous respiration of the guinea pig with Gallamin (2 mg/kg, i.v.), air was supplied to the snout side with an artificial respirator at the frequency of 70 times/min, and the flow rate of 4 ml air/time, and the atmospheric pressure required for the aeration was measured by the use of a transducer fitted at the branch. The measurement was used as a parameter of the nasal cavity resistance. The exposure of an antigen was carried out by generating aerosol of 3% OVA solution for 3 min between the respirator and the nasal cavity cannula. The test drug was administered orally 60 min before the antigen exposure. The intranasal pressure between 0 to 30 min was measured continuously and the effect was expressed as an inhibition rate to that obtained for vehicle using the AUC for 30 min (on the vertical axis, intranasal pressure (cm $H_2O$), and on the horizontal axis, time (0–30 min)) as an indication. The result is shown in Table 13.

TABLE 13

| Compd. No. | Inhibitory Rate (%) |
|---|---|
| IA-a-1 | 80 |

Experiment 4 Activity on infiltration of eosionophils in the nasal cavity by an antigen challenge To a Hartley male guinea pig was injected intraperitoneally cyclophosphamide (30 mg/kg), after 2 day 1 ml of suspension containing 1 mg of ovalbumin (OVA) and 100 mg of aluminum hydroxide was injected intraperitoneally. After 3 weeks, 1 ml of mixture of OVA (10 μg) and aluminum hydroxide (100 mg) was intraperitoneally injected as additional immunization to sensitize systemically. After the lapse of 3 weeks, local sensitization, each 10 μl of 1% OVA solution was dripped in both nasal cavities four times at 2–4 day intervals. After 5–7 days from the final sensitization, nasal antigen challenge was performed by dripping 10 μl of 1% OVA solution to the guinea pigs in the both nasal cavity. Five hours after nasal challenge, the guinea pigs were exsanguinated under the anesthetization. The nasal airways were washed by infusing 10 ml of saline, and the washings were collected. The washings were centrifuged, the cell pellets were resuspended in 100 μl of saline, and the total cells were counted by the Türk stain. Then smear samples were prepared, and the cells were classified after the May-Grünwald-Giemsa stain. The eosinophil number was determined by multiplying the rate of eosinophils with the total cells. A test compound (IA-a-5) was suspended in 0.5% methyl cellulose, and administered orally at a dose of 1 mg/kg, 3 mg/kg, and 10 mg/kg, respectively, 1 hr before the antigen challenge. The result is shown FIG. 1.

We confirmed that from the above experiments 1 and 2, the compound of the present invention has a potent $PGD_2$-antagonistic activity; from the experiment 4, the compound of the present invention is confirmed to significantly suppress the infiltration of eosinophils; and from the experiment 3, the compound of the present invention is confirmed to be useful as a drug for treating nasal blockage.

INDUSTRIAL APPLICABILITY

The present invention provides $PGD_2$ antagonists and inhibitors for infiltration of eosinophils, useful as a drug for treating mast cell dysfunction-associated diseases such as systemic mastocytosis and disorder of systemic mast cell activation as well as tracheal contraction, asthma, allergic rhinitis, allergic conjunctivitis, urticaria, ischemic reperfusion injury, inflammation and atopic dermatitis.

We claim:
1. A compound of the formula (I):

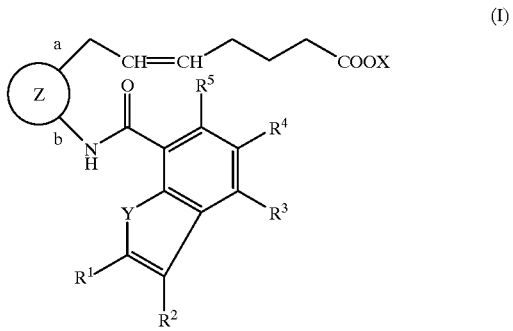

wherein

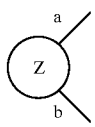

represents

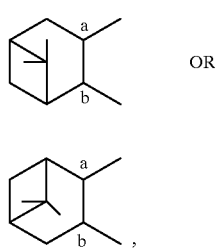

$R^1$, $R^2$, $R^3$, $R^4$ and $R^5$ represent independently hydrogen, alkyl, alkoxy, alkylthio, hydroxy, halogen, acyloxy or optionally substituted amino, or $R^1$ and $R^2$ may form an optionally substituted carbon ring together with the adjacent carbon atoms, $R^3$ and $R^4$ may form an optionally substituted carbon ring or an optionally substituted thiophene together with the adjacent carbon atoms, or $R^4$ and $R^5$ may form an optionally substituted carbon ring together with the adjacent carbon atoms, Y represents O or S, X represents hydrogen or alkyl, and the double bond on the α-chain has E configuration or Z configuration, pharmaceutically acceptable salt thereof, or hydrate thereof.

2. The compound as claimed in claim 1 represented by the formula (IA):

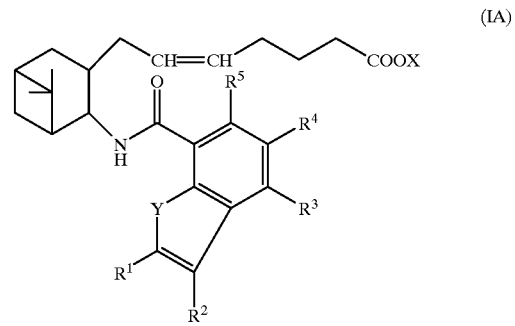

wherein $R^1$, $R^2$, $R^3$, $R^4$, $R^5$, Y and X are as defined above, and the double bond on the α-chain has E configuration or Z configuration, pharmaceutically acceptable salt thereof, or hydrate thereof.

3. The compound as claimed in claim 1 represented by the formula (IB):

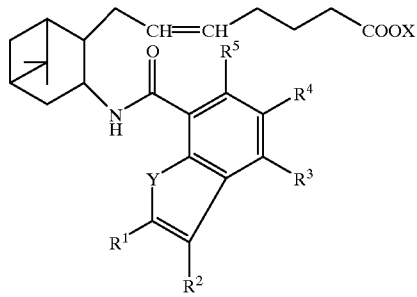

(IB)

wherein $R^1$, $R^2$, $R^3$, $R^4$, $R^5$, Y and X are as defined above, and the double bond on the α-chain has E configuration or Z configuration, pharmaceutically acceptable salt thereof, or hydrate thereof.

4. The compound as claimed in claim 2 represented by the formula (IA-a):

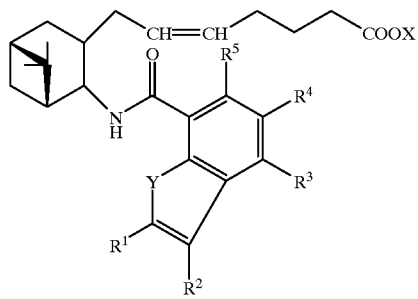

(IA-a)

wherein $R^1$, $R^2$, $R^3$, $R^4$, $R^5$, Y and X are as deffined above, and the double bond on the α-chain has E configuration or Z configuration, pharmaceutically acceptable salt thereof, or hydrate thereof.

5. The compound as claimed in claim 1, wherein $R^1$, $R^2$, $R^3$, $R^4$ and $R^5$ represent independently hydrogen, methyl, t-butyl, methylthio, methoxy, bromo, hydroxy, or acetoxy, pharmaceutically acceptable salt thereof, or hydrate thereof.

6. A compound of the formula (II):

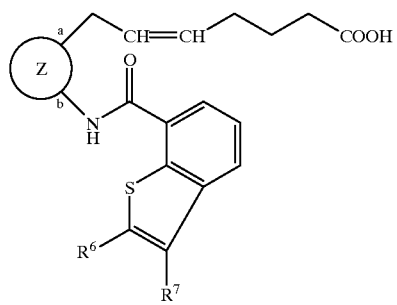

(II)

wherein

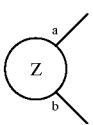

represents

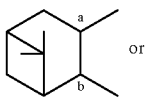

(A)

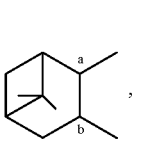

(B)

$R^6$ and $R^7$ represent independently hydrogen, alkyl, alkoxy, alkylthio, hydroxy, halogen, or acyloxy, and the double bond on the α-chain has E configuration or Z configuration, pharmaceutically acceptable salt thereof, or hydrate thereof.

7. The compound as claimed in claim 6 represented by the formula (IIA-a):

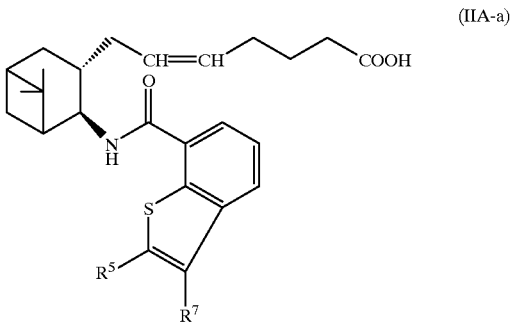

(IIA-a)

wherein $R^6$ and $R^7$ are as defined above, and the double bond on the α-chain has E configuration or Z configuration, pharmaceutically acceptable salt thereof, or hydrate thereof.

8. The compound as claimed in claim 6, wherein $R^6$ and $R^7$ represent independently hydrogen, methyl, t-butyl, methylthio, methoxy, bromo, hydroxy, or acetoxy, pharmaceutically acceptable salt thereof, or hydrate thereof.

9. A compound of the formula (III):

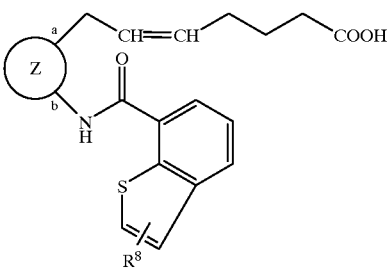

(III)

wherein

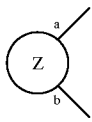

represents

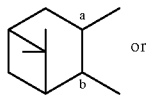 or

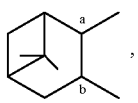

wherein $R^8$ represents hydrogen, alkyl, alkoxy, alkylthio, hydroxy, halogen, or acyloxy, and the double bond on the α-chain has E configuration or Z configuration, pharmaceutically acceptable salt thereof, or hydrate thereof.

10. The compound as claimed in claim 9 represented by the formula (IIIA-a):

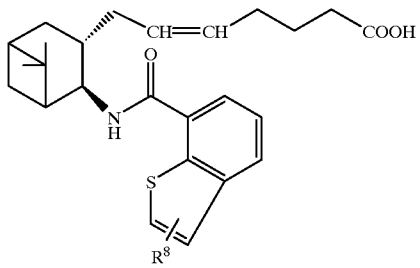

(IIIA-a)

wherein $R^8$ is as defined above, and the double bond on the α-chain has E configuration or Z configuration, pharmaceutically acceptable salt thereof, or hydrate thereof.

11. The compound as claimed in claim 9, wherein $R^8$ represents hydrogen, methyl, t-butyl, methylthio, methoxy, bromo, hydroxy, or acetoxy, pharmaceutically acceptable salt thereof, or hydrate thereof.

12. The compound, pharmaceutically acceptable salt thereof, or hydrate thereof as claimed in claim 1, wherein the double bond on the α-chain has E configuration.

13. The compound, pharmaceutically acceptable salt thereof, or hydrate thereof as claimed in claim 1, wherein the double bond on the α-chain has Z configuration.

14. A pharmaceutical composition comprising the compound, pharmaceutically acceptable salt thereof, or hydrate thereof as claimed in claim 1.

15. A pharmaceutical composition comprising the compound, pharmaceutically acceptable salt thereof, or hydrate thereof as claimed in claim 1 for use as $PGD_2$ antagonist.

16. A pharmaceutical composition inhibiting infiltration of inflammatory cells comprising the compound, pharmaceutically acceptable salt thereof, or hydrate thereof as claimed in claim 1 for use as $PGD_2$ antagonist.

17. The pharmaceutical composition as claimed in claim 16, wherein the inflammatory cells are eosionophils.

18. A pharmaceutical composition for treating nasal blockage comprising the compound, pharmaceutically acceptable salt thereof, or hydrate thereof as claimed in claim 1.

* * * * *